(12) United States Patent
Xie et al.

(10) Patent No.: US 8,555,498 B2
(45) Date of Patent: Oct. 15, 2013

(54) METHODS FOR MANUFACTURING AN IMPLANTABLE MEDICAL DEVICE

(75) Inventors: Jian Xie, Stevenson Ranch, CA (US); Kavous Sahabi, Winnetka, CA (US)

(73) Assignee: Pacesetter, Inc., Sylmar, CA (US)

( * ) Notice: Subject to any disclaimer, the term of this patent is extended or adjusted under 35 U.S.C. 154(b) by 933 days.

(21) Appl. No.: 12/695,068

(22) Filed: Jan. 27, 2010

(65) Prior Publication Data
US 2010/0132184 A1 Jun. 3, 2010

Related U.S. Application Data

(62) Division of application No. 11/290,921, filed on Nov. 29, 2005, now Pat. No. 7,729,769.

(51) Int. Cl.
*H01R 43/00* (2006.01)
*H05K 13/00* (2006.01)

(52) U.S. Cl.
USPC ............ 29/854; 29/592.1; 29/831; 29/844; 29/846; 29/858; 600/25; 600/372; 607/36; 607/37

(58) Field of Classification Search
USPC ............ 29/592.1, 831, 844, 846, 854, 858; 607/36, 37; 600/25, 372
See application file for complete search history.

(56) References Cited

U.S. PATENT DOCUMENTS

| | | | |
|---|---|---|---|
| 3,870,064 A * | 3/1975 | Vigneron | ............... 137/15.13 |
| 4,352,951 A | 10/1982 | Kyle | |
| 5,650,915 A * | 7/1997 | Alfaro et al. | ............... 361/707 |
| 6,529,103 B1 * | 3/2003 | Brendel et al. | ............ 333/182 |
| 6,879,857 B2 | 4/2005 | Swanson et al. | |
| 6,931,283 B1 | 8/2005 | Magnusson | |
| 7,260,434 B1 * | 8/2007 | Lim et al. | ................. 607/37 |
| 2004/0049239 A1 | 3/2004 | Swanson et al. | |
| 2005/0081291 A1 * | 4/2005 | Otten | ........................ 4/621 |
| 2005/0119709 A1 | 6/2005 | Gauglitz et al. | |

OTHER PUBLICATIONS

NonFinal Office Action (Restriction), mailed Dec. 22, 2008—Parent U.S. Appl. No. 11/290,921.
NonFinal Office Action, mailed Apr. 1, 2009—Parent U.S. Appl. No. 11/290,921.
NonFinal Office Action, mailed Apr. 21, 2009—Parent U.S. Appl. No. 11/290,921.
Notice of Allowance, mailed Jan. 13, 2010—Parent U.S. Appl. No. 11/290,921.

* cited by examiner

*Primary Examiner* — Paul D Kim

(57) ABSTRACT

A method for hermetically sealing electronic circuitry within a housing of an implantable medical device is provided. The method comprises assembling the housing having an interior cavity, joining a feed-through assembly to the housing, and joining a back-fill member to the feed-through housing. The back fill member has an opening there through communicating with the interior cavity of the housing. The housing is back-filled with an inert gas through the opening in the back-fill member, and the interior cavity is hermetically sealed by closing the opening through the back-fill member with a sealing element. The sealing element and back-fill member are formed of different first and second materials, respectively.

10 Claims, 9 Drawing Sheets

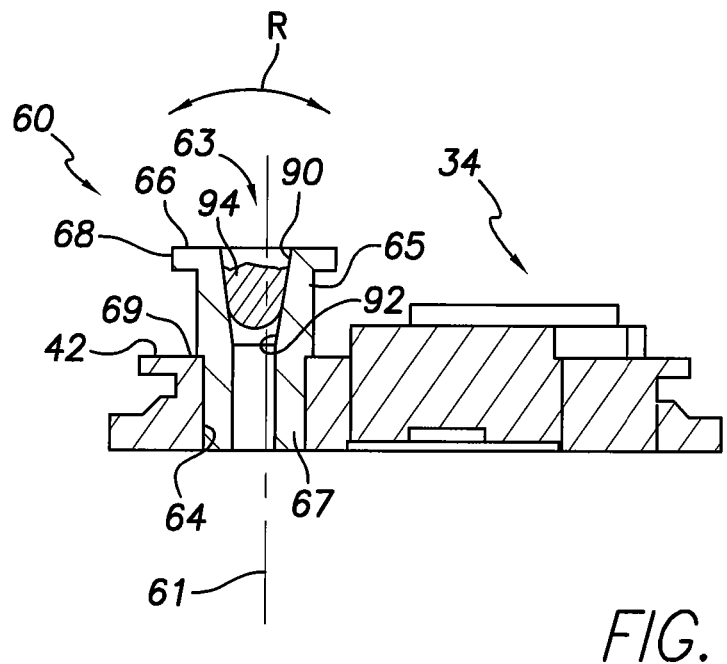
FIG. 7
FIG. 8
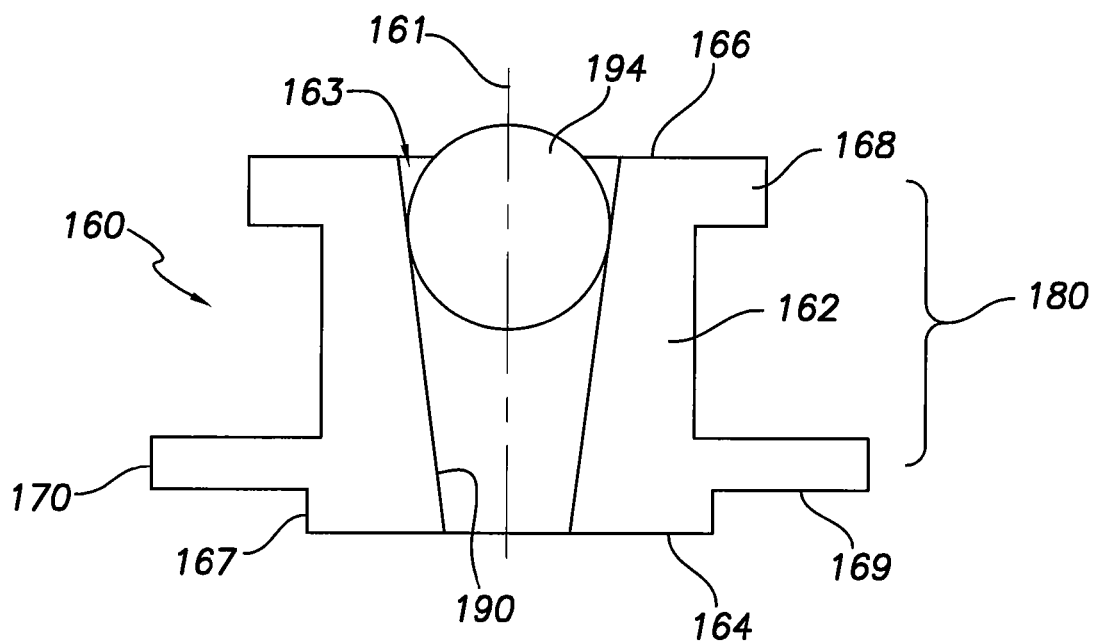

METHODS FOR MANUFACTURING AN IMPLANTABLE MEDICAL DEVICE

CROSS REFERENCE TO RELATED APPLICATIONS

This application is a division of U.S. patent application Ser. No. 11/290,921, filed Nov. 29, 2005.

FIELD OF THE INVENTION

This invention relates generally to implantable medical devices and methods of manufacturer thereof, and more particularly to methods and apparatus for hermetically sealing electronic circuitry within a housing of the implantable medical device.

BACKGROUND OF THE INVENTION

An implantable medical device is a medical device that is implanted in a patient to, among other things, monitor electrical activity of a heart and to deliver appropriate electrical and/or drug therapy, as required. Implantable medical devices (IMDs) include, for example, pacemakers, cardioverters, defibrillators, and the like. The electrical therapy produced by an IMD may include, for example, pacing pulses, cardioverting pulses, and/or defibrillator pulses. The IMD is used to both provide treatment for the patient and to inform the patient and medical personnel of the physiologic condition of the patient and the status of the treatment.

In general, implantable medical devices include a battery and electronic circuitry, such as a pulse generator and/or a processor module, that are hermetically sealed within a metal housing (generally referred to as the "can"). The metal housing typically is formed of titanium and includes opposed concave half shells that are welded together to form a device housing with an interior cavity, in which the battery, pulse generator and/or processor module reside. The half shells have an oval contour with a header receptacle area configured to receive a header assembly that is joined to the device housing. A feed-through assembly is located at the header receptacle area and is sealed to the half shells of the device housing to form an interface for conductors to enter/exit the interior cavity.

During manufacture, the battery and electronic circuitry are encased between the opposed half shells of the device housing and the half shells are welded to one another, such as through the use of laser welding, to form the IMD. Following the laser welding process, argon and/or helium gas may remain within the interior of the device case. Argon and helium gas exhibit low breakdown voltage characteristics (e.g., 12 volts/mil for argon and 4 volts/mil for helium). Thus, it may be preferable to remove the argon or helium gas from the completed implantable medical device. To remove the argon and helium gas, the device is placed in a nitrogen chamber and nitrogen gas, which has a higher break-down voltage (e.g., 81 volts/mil), is back-filled into the device case through a back-fill port provided in the device case. Upon completion of the nitrogen back-filling process, the back-fill port is temporarily sealed. The device case is then removed from the nitrogen chamber and into the back-fill port is permanently sealed.

However, conventional implantable medical devices and methods of manufacture have experienced certain limitations. Conventional manufacturing methods for joining feed-through assemblies and back-fill ports to a device case are unduly complex and costly. Further, once the device is removed from the nitrogen chamber, the nitrogen gas may leak out around the temporary seal before permanently sealed to the back-fill port. Also, when temporarily sealing the back-fill port, a support tool and a press tool are used. The support tool must fit into an area that has a very close tolerance, without interfering with the feed-through assembly, which makes the manufacturing process difficult, unpredictable and slow.

A need remains for an improved feed-through and back-fill configuration for an implantable medical device, and methods of manufacturer therefor.

SUMMARY

In accordance with certain embodiments, an implantable medical device is provided for implantation in a body. The device comprises a device housing having an interior cavity and electronic circuitry located in the interior cavity of the device housing. The electronic circuitry detects a physiologic condition of the body and delivers a therapy to the body. The device further includes a feed-through assembly having a feed-through housing that is joined to the device housing. The feed-through assembly includes conductors held in the feed-through housing and electrically connected to the electronic circuitry. A back-fill member is joined to the feed-through housing. The back-fill member has an opening there through communicating with the interior cavity of the device housing. A sealing element is hermetically secured in the opening through the back-fill member. The sealing element and back-fill member are formed of different first and second materials, respectively, where the second material forming the back-fill member is generally harder than the first material that forms the sealing element. For example, the sealing element may constitute a substantially pure titanium ball configured to be deformed when pressed into the opening in the back-fill member, where the first and second materials constitute titanium and a titanium alloy, respectively.

Optionally, the feed-through assembly may further comprise a ceramic conductor retention terminal held in, and joined to, the feed-through housing, the conductor retention terminal holding the conductors in a desired position. Optionally, the back-fill member may include a cylindrical body having ends located distal from and proximate to the feed-through housing, and a ledge extending about the proximate end of the body, where the ledge abuts against, and is sealed to, an exterior surface of the feed-through housing.

In accordance with an alternative embodiment, a method is provided for manufacturing an implantable medical device. The method comprises assembling a device housing having an interior cavity, joining a feed-through assembly to the device housing, where the feed-through assembly includes a feed-through housing and conductors held in the feed-through housing, and joining a back-fill member to the feed-through housing. The back fill member has an opening there through communicating with the interior cavity of the device housing. The method further comprises back-filling the device housing with an inert gas, having a relatively high breakdown voltage, through the opening in the back-fill member and sealing hermetically the interior cavity by closing the opening through the back-fill member with a seal element, where the sealing element and back-fill member are formed on different first and second materials, respectively.

Optionally, the sealing may further comprise holding the back-fill member with a support tool in a self-aligning manner, when closing the opening with the sealing element, which permits the back-fill member and device housing to self-align within the support tool while a press load is induced onto the sealing element. As a further option, the sealing may comprise retaining the back-fill member with a support tool that defines a support X-Y plane, inducing a press load onto the sealing element in a direction that intersects the X-Y plane and permitting the device housing to shift in at least one of the X-Y plane and a tilting direction out of the X-Y plane while the press load is induced.

BRIEF DESCRIPTION OF THE DRAWINGS

FIG. 7 illustrates a sectional view taken along line 7-7 in FIG. 5.

FIG. 8 illustrates a sectional view of a back-fill member formed in accordance with an alternative embodiment of the present invention with a sealing element initially placed in the opening.

DETAILED DESCRIPTION OF THE INVENTION

Figure 1:
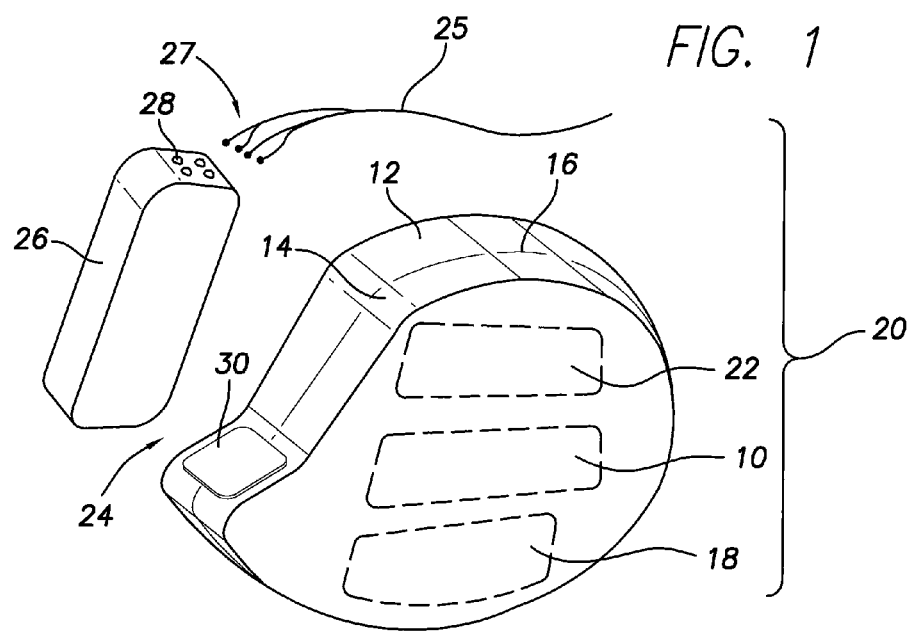
FIG. 1 illustrates an implantable medical device configured to utilize a feed-through assembly and a back-fill member formed in accordance with an embodiment of the present invention.

FIG. 1 illustrates an implantable medical device (IMD) 10 formed in accordance with an embodiment of the present invention. The IMD 10 includes opposed first and second half shells 12 and 14 that are joined with one another at an interface 16 (such as through laser welding) to form the device housing. The half shells 12 and 14 define an interior cavity there between that includes a battery 18 and electronic circuitry such as a pulse generator 20 and/or processor module 22 (generally denoted in dashed lines). The processor module 22 is located in the interior cavity of the device housing and operates to detect a physiologic condition of the body in which the device is implanted. The processor module 22 also delivers a therapy to the body (such as through delivery of a shock, pacing polls, electrical stimulus, delivery of a drug and the like). The pulse generator 20 may include one or more capacitors that store a pacing pulse or shocking energy. The half shells 12 and 14 have a contour that includes a header retention area 24 that is configured to receive a header assembly 26, to which one or more electrodes 25 and leads 27 (not shown) are attached at ports 28. The header retention area 24 includes an aperture 30 opening into the interior cavity of the half shells 12 and 14. The aperture 30 receives a feed-through assembly 32 (FIGS. 2-4) that is hermetically sealed to the half shells 12 and 14.

Figure 2:
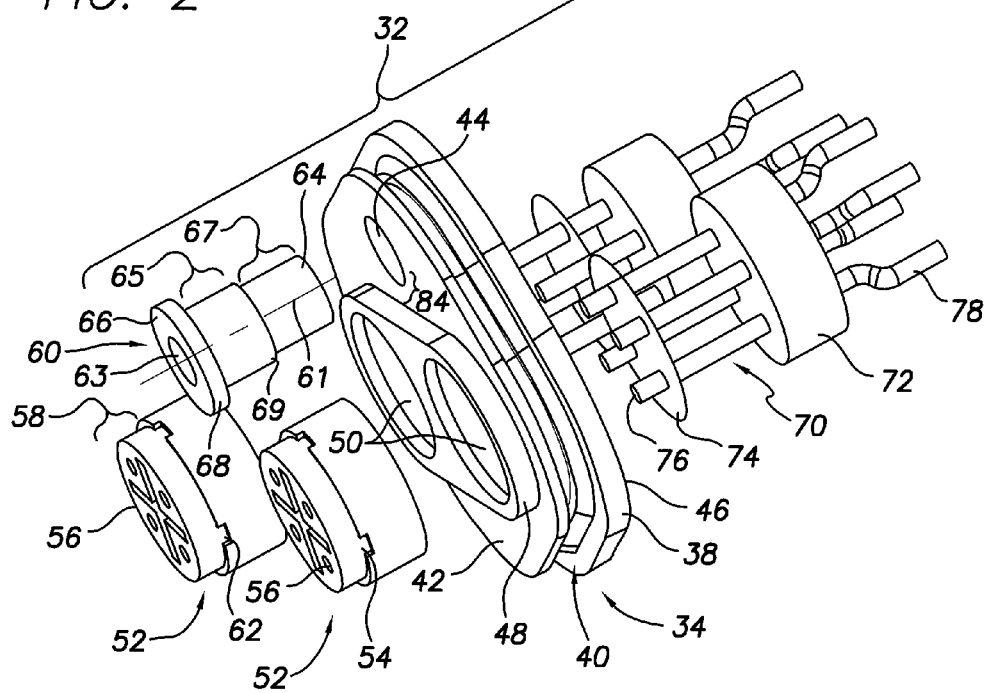
FIG. 2 illustrates an exploded isometric view of a feed-through assembly formed in accordance with an embodiment of the present invention.

FIG. 2 illustrates an exploded isometric view of the feed-through assembly 32. The feed-through assembly 32 includes a feed-through housing 34 having apertures 44 and 50 that extend between top and bottom surfaces 42 and 46. The aperture 44 receives a back-fill member 60, while the apertures 50 receive conductor retention terminals 52. The conductor retention terminals 52 may be formed of ceramic material and provided with channels 56 extending there through. The feed-through housing 34 is formed of a material capable of hermetically sealing with the material, from which the conductor retention terminals 52, is formed. For example, the feed-through housing 34 may be formed from substantially pure titanium and other materials suitable to be brazed to ceramic materials. The materials, from which the feed-through housing 34 may be formed, may vary depending upon the material utilized for the conductor retention terminals 52.

A ledge 54 is provided about each conductor retention terminal 52. The ledge 54 includes keying notches 62 that are joined with corresponding keying features internal to the apertures 50 in order to orient properly the conductor retention terminals 52. Individual conductors 70 are held in EMI capacitors 72 and polymide washers 74. The conductors 70 have exterior portions 76 that pass through the channels 56 in the conductor retention terminals 52. Interior portions 78 of the conductors 70 are electrically joined to the electronic circuitry within the IMD 10, such as the pulse generator 20 and processor module 22. The conductor retention terminals 52 are loaded into the apertures 50 from the bottom surface 46. An outer portion 58 of each conductor retention terminal 52 extends beyond the raised ledge 48.

The feed-through housing 34 is formed with a generally square plate shaped body. The feed-through housing 34 has a base flange 38 extending about a perimeter thereof. The feed-through assembly 32 is placed in or over aperture 30 in the IMD 10 and laser welded about the base flange 38 to half shells 10 and 12. A notch 40 is located above the base flange 38 and also extends about the perimeter of the feed-through housing 34. The top surface 42 includes the aperture 44 that extends through the feed-through housing 34 and opens onto the bottom surface 46. A raised ledge 48 extends upward from and machined integral with the top surface 42 of the feed-through housing 34. The raised ledge 48 is shaped to surround apertures 50 that extend through the feature housing 34 to the bottom surface 46. The raised ledge 48 forms a counter bore within the apertures 50 that fit against ledge 54 provided on the conductor retention terminals 52. The raised ledge 48 is located remote from the aperture 44. By way of example, the raised ledge 48 may be spaced a predetermined distance 84 from the nearest edge of the aperture 44.

The back-fill member 60 includes a generally cylindrical body having a proximal end 64 that is received in the aperture 44 and a distal end 66 that is located remote from the top surface 42 of the feed-through housing 34 when the back-fill member 60 is fully installed. The back-fill member 60 may be generally tubular in shape, extending along a longitudinal axis 61, with a flange 68 formed about the distal end 66. The flange 68 extends outward in a radial direction from the longitudinal axis 61. The back-fill member 60 includes an opening 63 extending therethrough between the proximal and distal ends 64 and 66. The opening 63 communicates with the interior cavity of the IMD 10 to enable back-filling of an inert gas (e.g., nitrogen) during the manufacturing process. An exterior surface of the back-fill member 60 is segmented into upper and lower portions 65 and 67 having different diameters and being separated by a ledge 69 there between.

Figure 3:
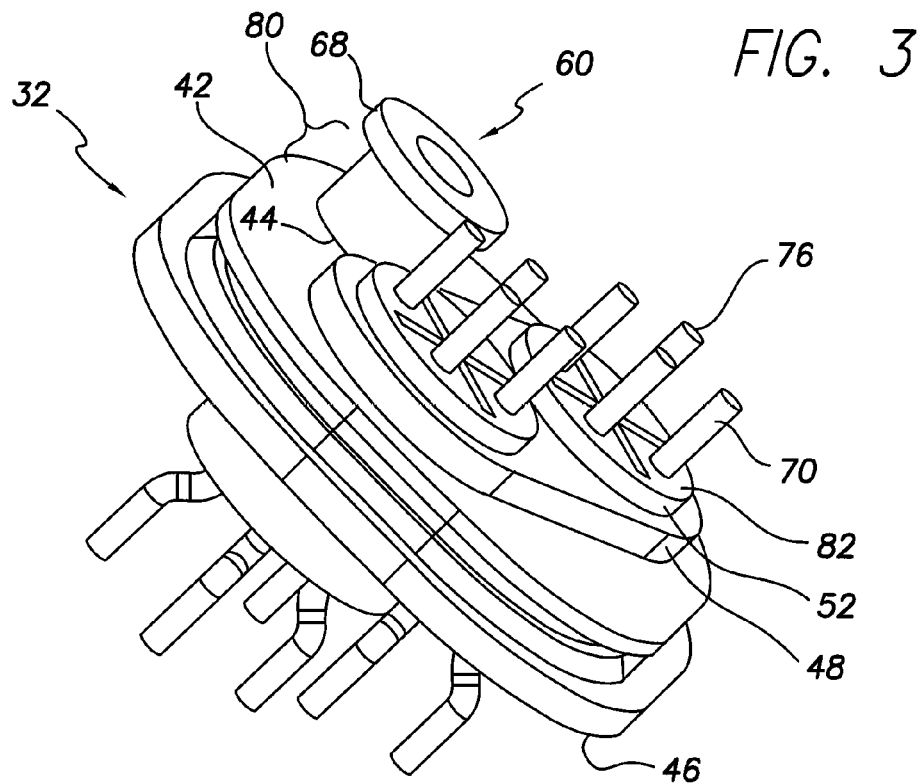
FIG. 3 illustrates a top isometric view of the feed-through assembly of FIG. 2.

FIG. 3 illustrates a top isometric view of the feed-through assembly 32 once fully assembled. As shown in FIG. 3, once the back-fill member 60 is fully loaded into the aperture 44, the lower surface of the flange 68 is spaced a distance 80 above the top surface 42 of the feed-through housing 34. The conductor retention terminals 52 are loaded upward from the bottom surface 46 into the feed-through housing 34 to hold conductors 70 in place with exterior portions 76 extending outward beyond the top surface 82 of the conductor retention terminals 52. The exterior portions 76 may very in length and be much longer than shown in FIG. 3.

Figure 4:
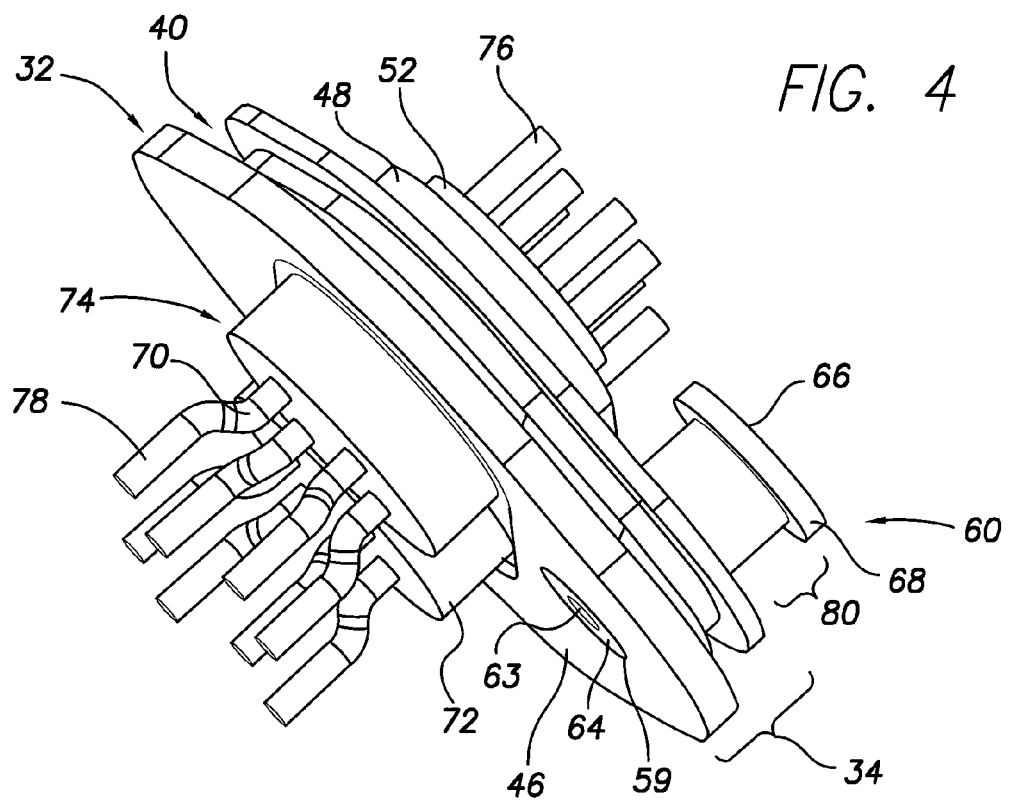
FIG. 4 illustrates a bottom isometric view of the feed-through assembly of FIG. 2.

FIG. 4 illustrates a bottom isometric view of the feed-through assembly 32. The proximal end 64 of the back-fill member 60 is positioned flush with the bottom surface 46 of the feed-through housing 34 and is laser welded at interface 59. The flange 68 at the distal end 66 of the back-fill member 60 is spaced the distance 80 from the top surface 42 of the feed-through housing 34. The opening 63 extends through the back-fill member 60 to communicate with the interior of the IMD 10 when the feed-through assemblies 32 is sealably joined to the device housing. Interior portions 78 of the conductors 70 and the EMI capacitors 72 extend downward from the bottom of the feed-through housing 34. The interior portions 78 may also vary in length and be much longer than shown in FIG. 4.

Figure 5:
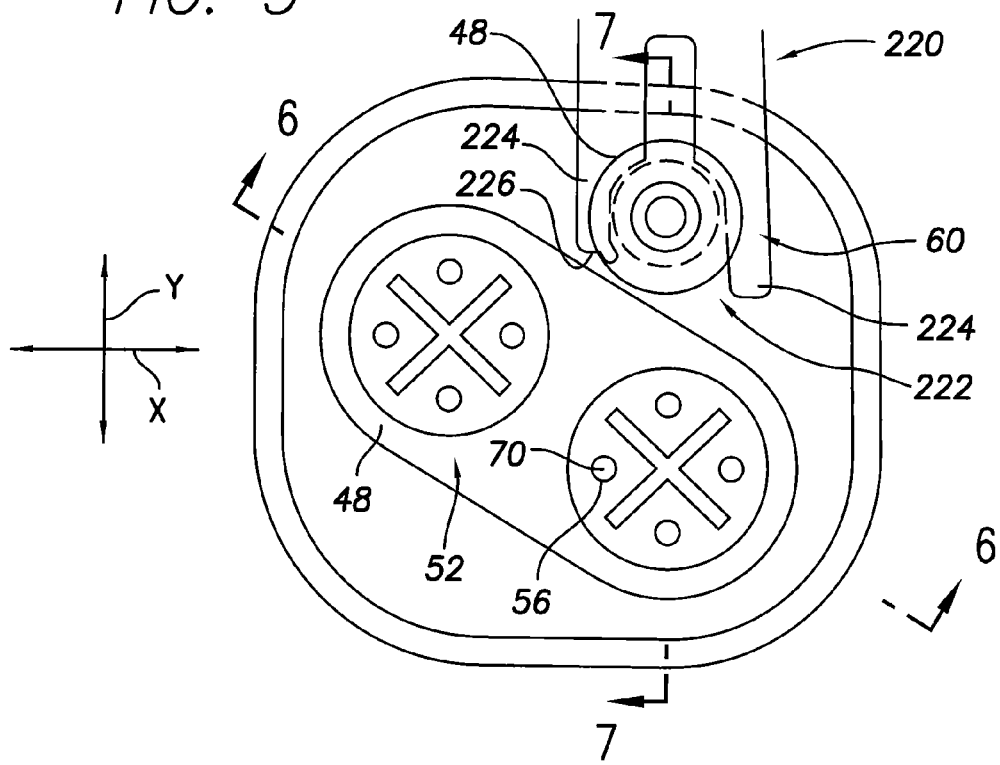
FIG. 5 illustrates a top plan view of the feed-through assembly of FIG. 2 engaged with a portion of a support tool.

FIG. 5 illustrates a top plan view of the feed-though assembly 32 with the back-fill member 60 located separate and apart from the raised ledge 48 surrounding the conductor retention terminals 52. The conductor retention terminals 52 are brazed about perimeter 53 to the raised ledge 48. In the exemplary embodiment, each conductor retention terminal 52 includes four channels 56, each of which holds a single conductor 70. In the exemplary embodiment, a pair of conductor retention terminals 52 are included and positioned along an axis extending between opposed diagonal corners of the feed-through housing 34. The back-fill member 60 is spaced such that the outer perimeter of the flange 68 does not overlap the raised ledge 48.

As explained below in more detail, a support tool 220 may engage the backfill member 60 during the sealing operation. The support tool 220 includes forks 224 separated by an aperture 222 that is fit around the body of the back-fill member 60. As shown in FIG. 5, the outer ends 226 of the forks 224 stop before interfering with or engaging the raised ledge 48.

Figure 6:
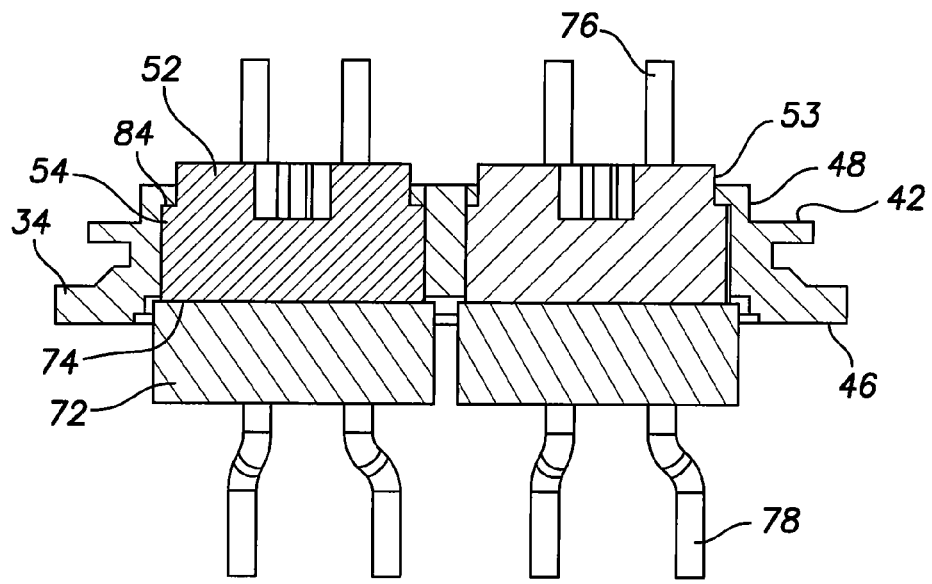
FIG. 6 illustrates a sectional view taken along line 6-6 in FIG. 5.

FIG. 6 illustrates a side sectional view taken along line 6-6 in FIG. 5. The conductor retention terminals 52 are loaded through the bottom of the feed-though housing 34 until the ledges 54 abut against counterbores 84. The conductor retention terminals 52 are followed by the washers 74 that are followed by the EMI capacitors 72. The conductor retention terminals 52 are hermetically sealed about the perimeters 53 to the raised ledge 48 through brazing. The conductors 70 are hermetically sealed and secured within the channels 56 (FIG. 5).

FIG. 7 illustrates a side sectional view taken along line 7-7 in FIG. 5 showing how the back-fill member 60 is held in the feed-through housing 34. The lower portion 67 of the back-fill member 60 is inserted in through the top of the aperture 44 until the ledge 69 abuts against the top surface 42 of the feed-through housing 34. The lower portion 67 has a length substantially equal to the thickness of the feed-through housing 34. The upper portion 65 has a length sufficient to afford a desired amount of tolerance for a support tool 220 (FIG. 5)

used when sealing the opening 63. The opening extends along an axis 61. The opening 63 through the back-fill member 60 is tapered to present a tapered surface 90 beginning with a larger diameter proximate the distal end 66 and reducing to a smaller diameter at an intermediate point 92 within the opening 63. The intermediate point 92 may be aligned generally with the top surface 42 of the feed-through housing 34. Below the intermediate point 92, the opening 63 is generally of even diameter. The tapered surface 90 may be polished.

In FIG. 7, the opening 63 includes a sealing element 94 that has been pressed into the opening 63 to a deformed state and below the surface of the distal end 66. By way of example, the sealing element 94 may constitute a titanium ball or the like that is loaded into the opening 63 following completion of the back-fill process. A load is induced upon the sealing element 94, such as with a press tool to force the sealing element 94 downward into the opening 63 along the tapered surface 90 until achieving a desired degree of hermetic seal.

The back-fill member 60 may be formed of a material that differs from the material used to form the feed-through housing 34. For example, the back-fill member 60 may be formed of a titanium alloy and the like. The sealing member 94 may be formed of a material the same or similar to the feed-through housing 34 (e.g., titanium and the like). The back-fill member 60 is formed of a material harder than the sealing element 94 such that, when the sealing element 94 is placed under a sufficient load, the sealing element 94 deforms, while the back-fill member 60 does not substantially deform. Further, the materials used to form the back-fill member 60 and the sealing element 94 may be compatible for bonding with one another, such as through welding and the like.

FIG. 8 illustrates a side sectional view of a backfill member 160 formed in accordance with an alternative embodiment. The backfill member 160 includes a tubular body portion 162 extending along a longitudinal axis 161 between a proximal end 164 and a distal end 166. A platform 170 extends about the body 162 proximate the proximal end 164 to define a ledge 169 above a lip 167 that is received in the aperture 44 (FIG. 2). The ledge 169 may rest against the top surface of the can or against the top surface 42 of the feed-through housing 34. A flange 168 is provided at the distal end 166 and is spaced a distance 180 above the platform 170. The backfill member 160 includes an opening 163 extending therethrough. The opening 163 includes a polished interior surface 190 that is tapered along its entire length. A sealing element 194 is shown in an initial position when first inserted into the opening 163 at the distal end 166. In the example of FIG. 8, the sealing element 194 represents a titanium ball.

Figure 9:
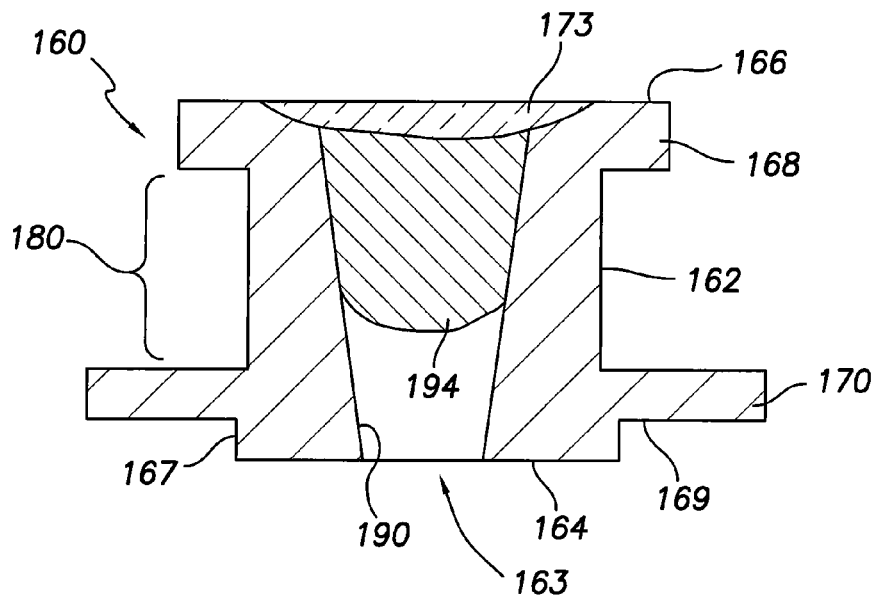
FIG. 9 illustrates a sectional view of the backfill member of FIG. 8 with the sealing element pressed, deformed and permanently sealed therein.

FIG. 9 illustrates a side sectional view of the backfill member 160 of FIG. 8, following completion of a pressing operation during which a load is induced upon the sealing element 194. The sealing element 194 is deformed into a conically shape conforming to the tapered interior surface 190 of the backfill member 160. A portion 173 of the distal end 166 and the sealing element 194 are shown to be laser welded to one another to achieve a permanent hermetic seal.

Optionally, the back-fill member may be machined integral with the feed-through housing, and thus formed of a common material (e.g., a titanium alloy). In this alternative embodiment, the raised ledge may be formed as a separate and distinct piece and made of a material (e.g., substantially pure titanium) that differs from the material, from which the feed-through housing is made. The separate raised ledge would then be inserted into a large oval aperture through the feed-through housing 34 and joined (e.g., laser welded) to the feed-through housing. The raised ledge would still receive and be joined (e.g., brazed) to the conductor retention terminals.

Figure 10:
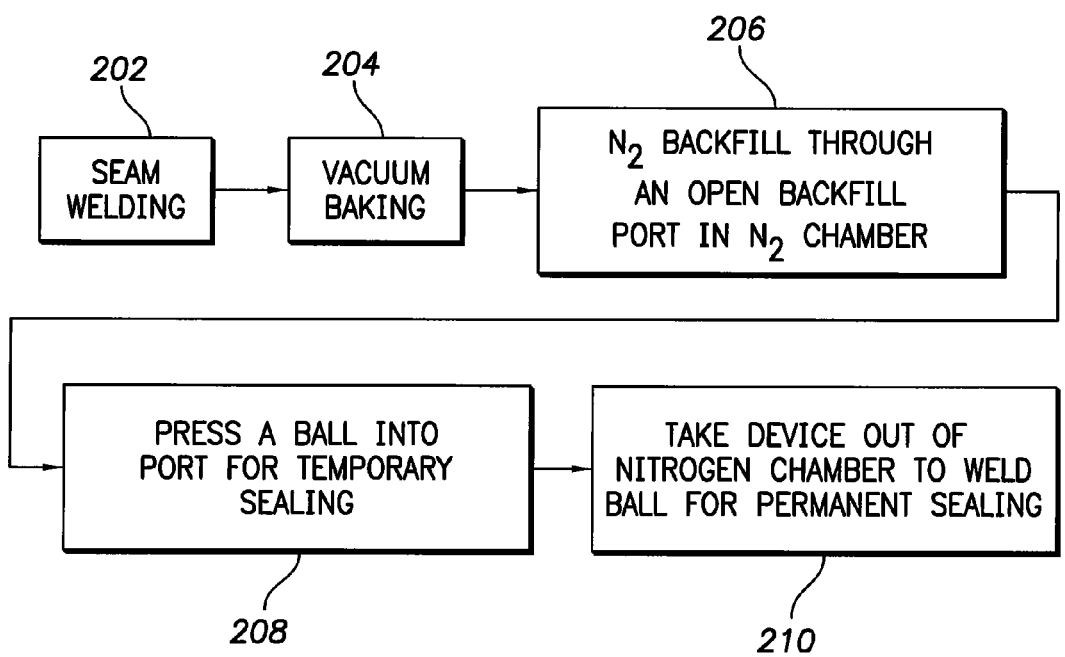
FIG. 10 illustrates a block diagram of a flow process for nitrogen filling an implantable medical device in accordance with an embodiment of the present invention.

FIG. 10 illustrates a block diagram of a flow process for nitrogen filling an implantable medical device. The process 200 begins at 202, where the half shells are joined and seam welded to one another with the battery and electronic components therein. At 204, the device undergoes vacuum baking. At 206, nitrogen is back-filled through the opening in the back-fill member while the device is held in a nitrogen chamber. At 208, while the device remains in the nitrogen chamber, a sealing element (e.g. a ball) is pressed into the distal end of the backfill member sufficiently to temporarily seal the opening through the backfill member. At 210, the device is removed from the nitrogen chamber and the sealing element is permanently sealed within the opening of the backfill member (such as through welding). During 208, the back-fill member is permitted to linearly shift and/or tilt while a sealing force is applied to the sealing element to deform the sealing element into the opening in the back-fill member.

Figure 11:
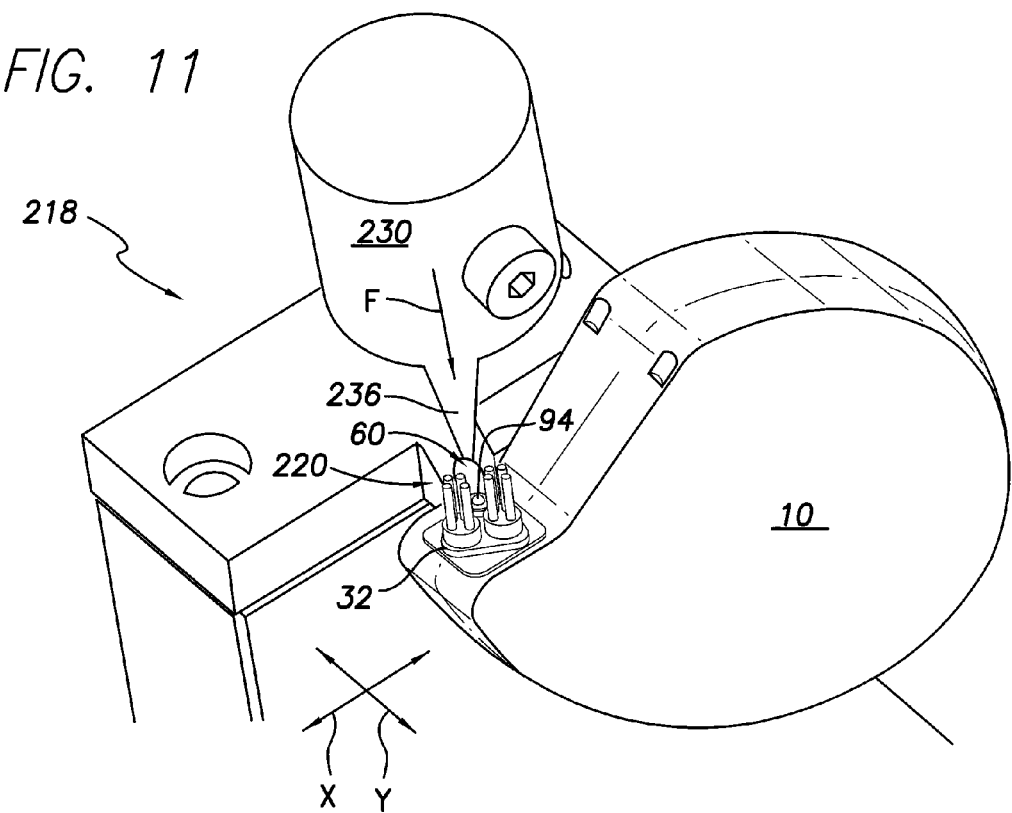
FIG. 11 illustrates a computer-generated model of an implantable medical device held within a pressing station in accordance with an embodiment of the present invention.

FIGS. 11 and 12A-12D illustrate computer-generated models of an implantable medical device 10 held within a pressing station 218, such as used at 208 during the method of FIG. 10, to temporarily seal a sealing element 94 in the opening of the backfill member 60. As shown in FIG. 11, the pressing station 218 includes the support member 220 and a pressing tool 230. The implantable medical device 10 is held by the support member 220. As better shown in FIG. 5, the support member 220 includes a forked support having a pair of forks 224 with an aperture 222 located therebetween. The forks 224 define a support X-Y plane extending parallel to, and including, upper surfaces of the forks 224. The pressing tool 230 induces a pressing force along a direction denoted by the arrow F in FIG. 11. The force F is generally applied perpendicular to the support X-Y plane.

Figure 12A:
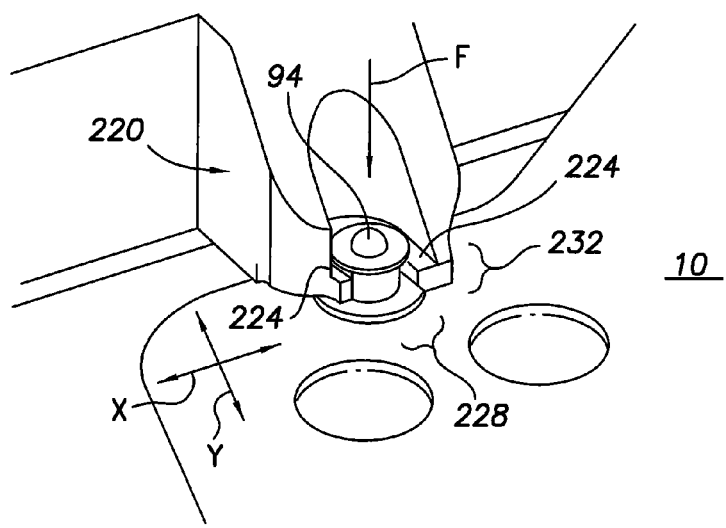
FIGS. 12A-12D illustrate computer generated models of the implantable medical device of FIG. 11 as self-aligned to various positions within the pressing station.
Figure 12B:
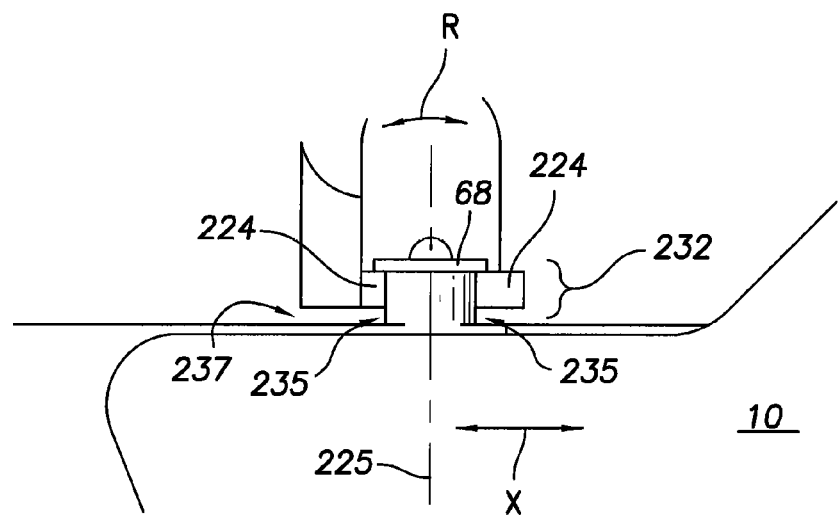

As shown in FIGS. 12A-12D, the forks 224 have an open outer face and interior facing surfaces that are spaced apart by a distance 228 that is greater than an outer diameter of the body of the backfill member 60. The forks 224 are configured to fit along opposite sides of the body of the backfill member below the flange 68. Each fork 224 has a vertical thickness 232 that is less than the distance 80 (FIG. 4) of the flange 68 above the top surface 42 (FIG. 3) of the feed-through housing 34 to provide a vertical tolerance 237 (FIG. 12B).

Figure 12C:
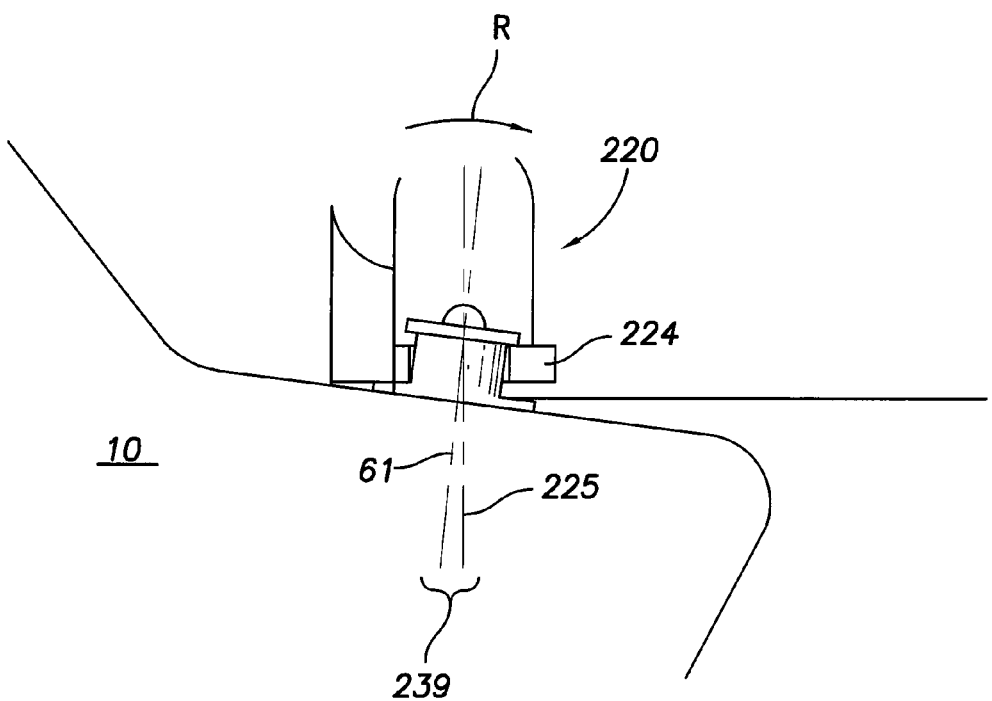
Figure 12D:
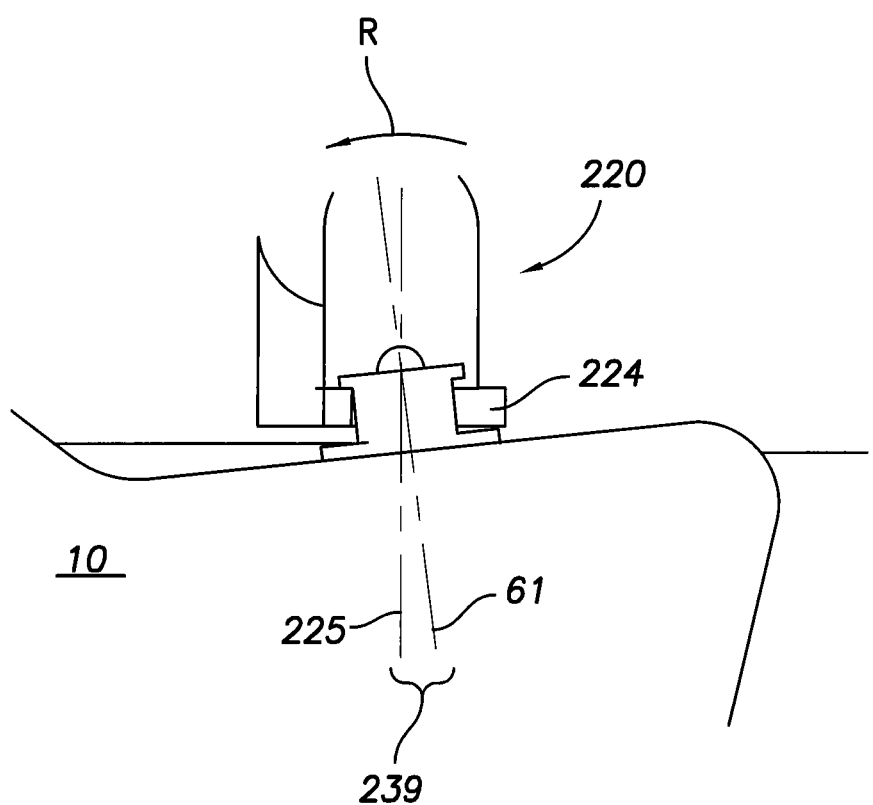

Returning to FIG. 11, once the support member 220 is properly positioned about the backfill member 60, a pressed tool 230 is moved downward until a press tip 236 engages the sealing element 94 positioned at the opening of the backfill member 60. The press tip 236 induces a predetermined load force onto the sealing element 94. The press tip 236 may not necessarily initially be centered over the sealing element 94. Thus, as the load is induced, the sealing element 94 undergoes a certain amount of lateral force, such as within the support X-Y plane and/or about a tilt axis out of the X-Y plane. The X-Y plane is illustrated by the arrows X and Y. The backfill member 60 may shift within the X-Y plane relative to the support member 220 (up to a predefined limit) for the sealing element 94 to become self-aligned with the press tip 236. The backfill member 60, and the entire IMD 10, may also tilt by an amount 239 (as shown by arc R in FIGS. 12B-12D) within the forks 224 such that the axis 61 of the opening 63 forms an acute angle with the vertical axis 225. In the examples of FIGS. 12C and 12D, the IMD 10 is tilted to opposite different first and second tilt limits relative to the forks 224. The tilt limits collectively form a tilt tolerance out of the support X-Y plane.

Figure 13:
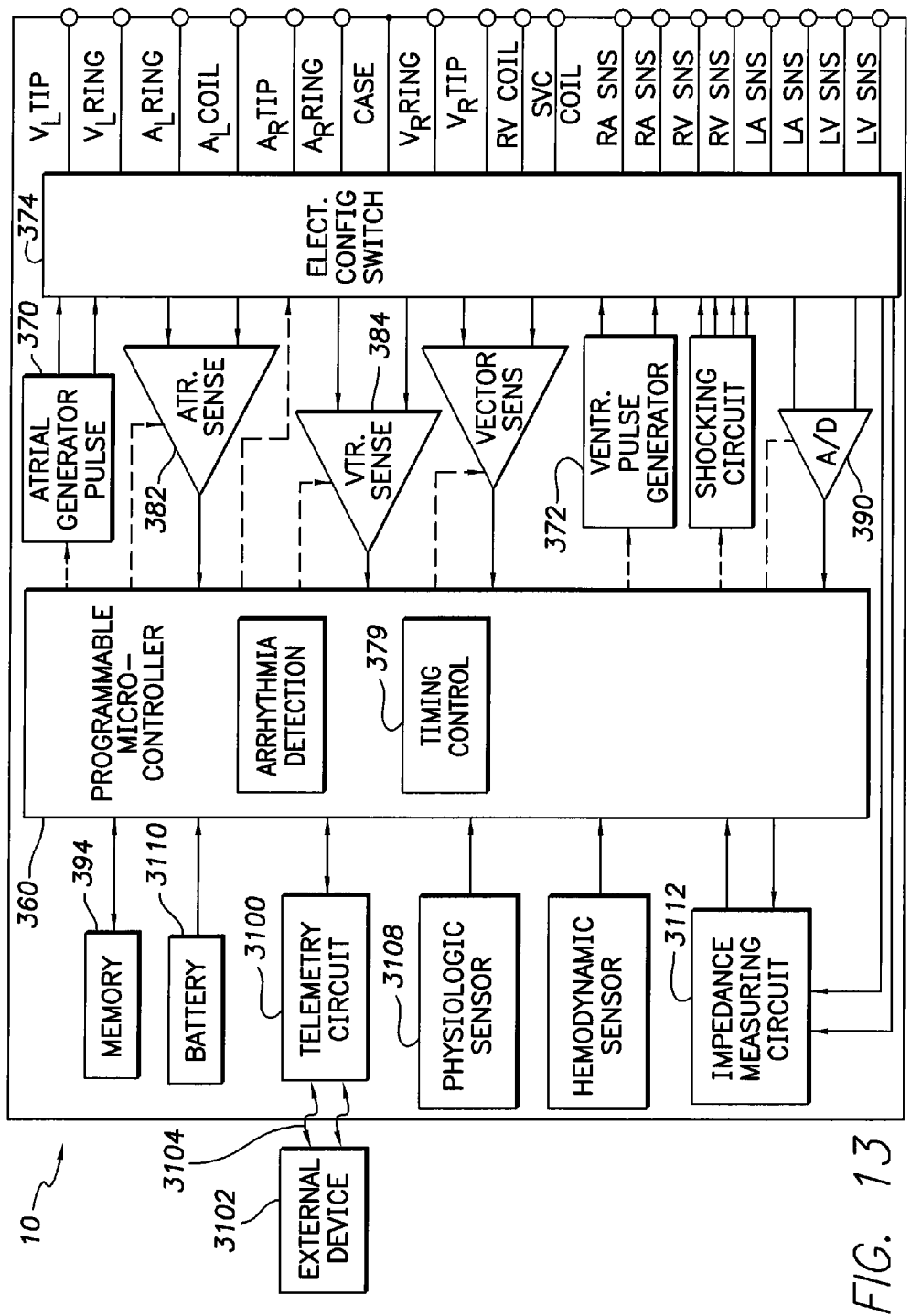
FIG. 13 illustrates a block diagram of electronic circuitry implemented within an implantable medical device.

FIG. 13 illustrates a block diagram the electronic circuitry for the implantable medical device 10. An atrial pulse generator 370 and ventricular pulse generator 372 generate stimulation pulses for delivery by the right atrial lead, the right ventricular lead, and/or the coronary sinus lead via a switch 374. It is understood that in order to provide stimulation therapy in each of the four chambers of the heart, the atrial pulse generator 370 and the ventricular pulse generator 372 may include dedicated, independent pulse generators, multiplexed pulse generators, or shared pulse generators. The atrial pulse generator 370 and the ventricular pulse generator 372 are controlled by the microcontroller 360 to trigger or inhibit the stimulation pulses.

The microcontroller 360 further includes timing control circuitry 379 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc. The switch 374 includes a plurality of switches for connecting the desired electrodes to the appropriate I/O circuits, thereby providing complete electrode programmability. Accordingly, the switch 374 determines the polarity of the stimulation pulses (e.g. unipolar, bipolar, cross-chamber, etc.) by selectively closing the appropriate combination of switches (not shown) as is known in the art. Atrial sensing circuits 382 and ventricular sensing circuits 384 may also be selectively coupled to the right atrial lead, coronary sinus lead, and the right ventricular lead, through the switch 374, for detecting the presence of cardiac activity in each of the four chambers of the heart. Accordingly, the atrial and ventricular sensing circuits 382 and 384 may include dedicated sense amplifiers, multiplexed amplifiers, or shared amplifiers. The switch 374 determines the "sensing polarity" of the cardiac signal by selectively closing the appropriate switches. In this way, the clinician may program the sensing polarity independent of the stimulation polarity.

Each of the atrial sensing circuit 382 or the ventricular sensing circuit 384 preferably employs one or more low power, precision amplifiers with programmable gain and automatic gain or sensitivity control, bandpass filtering, and a threshold detection circuit, to selectively sense the cardiac signal of interest. The automatic sensitivity control enables the IMD 10 to deal effectively with the difficult problem of sensing the low amplitude signal characteristics of atrial or ventricular fibrillation. The outputs of the atrial and ventricular sensing circuits 382 and 384 are connected to the microcontroller 360 for triggering or inhibiting the atrial and ventricular pulse generators 370 and 372, respectively, in a demand fashion, in response to the absence or presence of cardiac activity, respectively, in the appropriate chambers of the heart. For arrhythmia detection, the stimulation device 10 utilizes the atrial and ventricular sensing circuits 382 and 384 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 360 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.), in order to determine the type of remedial therapy that is needed (e.g. bradycardia pacing, anti-tachycardia stimulation, cardioversion shocks or defibrillation shocks, collectively referred to as "tiered therapy").

Cardiac signals are also applied to the inputs of a data acquisition system 390, which is depicted as an analog-to-digital (A/D) converter for simplicity of illustration. The data acquisition system 390 is configured to acquire intracardiac electrogram (EGM) signals, convert the raw analog data into digital signals, and store the digital signals for later processing and/or telemetric transmission to an external device 3102. The data acquisition system 390 is coupled to the right atrial lead, the coronary sinus lead, and the right ventricular lead through the switch bank 374 to sample cardiac signals across any pair of desired electrodes. The microcontroller 360 is further coupled to a memory 394, wherein the programmable operating parameters used by the microcontroller 360 are stored and modified, as required, in order to customize the operation of the IMD 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart within each respective tier of therapy.

The operating parameters of the IMD 10 may be non-invasively programmed into the memory 394 through a telemetry circuit 3100 in telemetric communication with the external device 3102, such as a programmer, transtelephonic transceiver, or a diagnostic system analyzer. The telemetry circuit 3100 is activated by the microcontroller 360. The telemetry circuit 3100 allows intracardiac electrograms and status information relating to the operation of the IMD 10 to be sent to the external device 3102 through the established communication link 3104. The IMD 10 includes a physiologic sensor 3108, commonly referred to as a "rate-responsive" sensor because it is typically used to adjust stimulation rate according to the exercise state of the patient. However, the physiological sensor 3108 may further be used to detect changes in cardiac output, changes in the physiological condition of the heart, or diurnal changes in activity (e.g. detecting sleep and wake states). Accordingly, the microcontroller 360 responds by adjusting the various stimulation parameters, such as the rate at which the atrial and ventricular pulse generators 370 and 372 generate stimulation pulses. In accordance with the present invention inter-chamber stimulation delays will be adjusted appropriately as the rate is adjusted.

The IMD 10 additionally includes a power source such as a battery 3110 that provides operating power to all the circuits shown. The IMD 10 may include an impedance measuring circuit 3112 which is enabled by the microcontroller 60 by means of a control signal 114. If it is a function of the IMD 10 to operate as an implantable cardioverter/defibrillator (ICD) device, it will detect the occurrence of an arrhythmia, and automatically apply an appropriate electrical stimulation or shock therapy to the heart aimed at terminating the detected arrhythmia.

It is understood that the modules, units and blocks illustrated are conceptual representations of certain features and functions. Each of the illustrated modules, units and blocks may be located in a common or in separate housings and may be joined to one another through wired or wireless connections. In addition, and the units may be implemented with hardware, software, firmware, as discrete components, as integrated components, with one or more processors, with one or more controllers, and any combination thereof.

While the invention has been described in terms of various specific embodiments, those skilled in the art will recognize that the invention can be practiced with modification within the spirit and scope of the claims.

What is claimed is:

1. A method for manufacturing an implantable medical device, comprising:
    assembling a device housing defining an interior cavity;
    joining a feed-through assembly to the device housing, the feed-through assembly including a feed-through housing and conductors held in the feed-through housing;
    joining a back-fill member to the feed-through housing, the back fill member having an opening there through communicating with the interior cavity of the device housing;
    back-filling the device housing with an inert gas through the opening in the back-fill member; and
    hermetically sealing the interior cavity by closing the opening through the back-fill member with a sealing element, where the sealing element and back-fill member are formed of different first and second materials, respectively;
    wherein the sealing further comprises holding the back-fill member in a support tool in a self-aligning manner when closing the opening with the sealing element, while permitting the back-fill member and device housing to self-align within the support tool while a press load is induced onto the sealing element.

2. The method of claim 1, further comprising loading a ceramic terminal into an aperture provided through the feed-through housing, and loading the conductors into the ceramic terminal.

3. The method of claim 1, wherein the first material constitutes titanium and the second material constitutes a titanium alloy.

4. The method of claim 1, wherein the sealing element constitutes a titanium ball and the sealing operation deforms the titanium ball when pressed into the opening in the back-fill member.

5. The method of claim 1, further comprising brazing a terminal holding the conductors to the feed-through housing.

6. A method for manufacturing an implantable medical device, comprising:
    assembling a device housing defining an interior cavity;
    joining a feed-through assembly to the device housing, the feed-through assembly including a feed-through housing and conductors held in the feed-through housing;
    joining a back-fill member to the feed-through housing, the back fill member having an opening there through communicating with the interior cavity of the device housing;
    back-filling the device housing with an inert gas through the opening in the back-fill member; and
    hermetically sealing the interior cavity by closing the opening through the back-fill member with a sealing element, where the sealing element and back-fill member are formed of different first and second materials, respectively;
    wherein the sealing further comprises retaining the back-fill member with a support tool that defines a support X-Y plane, inducing a press load onto the sealing element in a direction that intersects the X-Y plane and permitting the device housing to shift in at least one of the X-Y plane and a tilting direction out of the X-Y plane while the press load is induced.

7. The method of claim 6, wherein the back-filling is performed while the device housing is in a nitrogen chamber and the inert gas is nitrogen.

8. A method for manufacturing an implantable medical device, comprising:
- assembling a device housing defining an interior cavity;
- joining a feed-through assembly to the device housing, the feed-through assembly including a feed-through housing and conductors held in the feed-through housing;
- joining aback-fill member to the feed-through housing, the back fill member having an opening there through communicating with the interior cavity of the device housing;
- back-filling the device housing with an inert gas through the opening in the back-fill member; and
- hermetically sealing the interior cavity by closing the opening through the back-fill member with a sealing element, where the sealing element and back-fill member are formed of different first and second materials, respectively;
- wherein the sealing permits the back-fill member to at least one of linearly shift and tilt while a sealing force is applied to the sealing element to deform the sealing element into the opening in the back-fill member.

9. The method of claim 8, further comprising polishing an interior surface of the opening through the back-fill member prior to the sealing.

10. The method of claim 8, further comprising forming the back-fill member with a cylindrical body having distal and proximal ends relative to the feed-through housing, and a base platform extending about the body proximate the proximal end, the base platform abutting against, and being sealed to, an exterior surface of the feed-through housing during the joining.

* * * * *